US00PP17914P2

(12) United States Plant Patent
Lee et al.

(10) Patent No.: US PP17,914 P2
(45) Date of Patent: Aug. 14, 2007

(54) APPLE TREE NAMED 'CABP FUJI'

(50) Latin Name: *Malus Mill.*
Varietal Denomination: CABp Fuji

(75) Inventors: Chris Lee, Ongo Onga (NZ); Brian Edwards, Waipawa (NZ); Allan Delugar, Waipawa (NZ)

(73) Assignee: CABp 4 Limited, Waipawa (NZ)

( * ) Notice: Subject to any disclaimer, the term of this patent is extended or adjusted under 35 U.S.C. 154(b) by 261 days.

(21) Appl. No.: 10/943,785

(22) Filed: Sep. 17, 2004

Related U.S. Application Data

(60) Provisional application No. 60/504,129, filed on Sep. 19, 2003.

(51) Int. Cl.
*A01H 5/00* (2006.01)

(52) U.S. Cl. ..... Plt./168
(58) Field of Classification Search ..... Plt./168
See application file for complete search history.

(56) References Cited

PUBLICATIONS

UPOV ROM GTITIM Computer Database, GTI Jouve Retrieval Software 2005/03 Citation for 'Fuji Supreme'.*

Mannering, Rose "Sharp Eye Leads to Exciting Fuji Find" The Orchardist, New Zealand Fruitgrowers Federation 2004, available at: http://www.fruitgrowers.org.nz/orchardist/articles/2004/Apr. 22.htm.*

Anonymous. "New Cultivar from Fuji Sent for Export" HortNews, NZPA, 05, 17, 2005, available at: http://www.hortnet.co.nz/news/2004/n4757.htm.*

* cited by examiner

*Primary Examiner*—Wendy Haas
(74) *Attorney, Agent, or Firm*—Statton Ballew PLLC

(57) ABSTRACT

'CABp Fuji' is a new and distinct apple tree notable for its large, attractive fruit, having a pronounced stripe and superior color as compared to its parent 'Nagafu-6' and other known cultivars.

3 Drawing Sheets

Latin name of the genus and species of the plant claimed: *Malus* Mill.
Variety denomination: 'CABp Fuji'.

BACKGROUND OF THE INVENTION

The new cultivar originated as a limb sport mutation of a 'Nagafu-6' (unpatented) Fuji apple tree. It was discovered by the inventor in 1994 in a cultivated orchard at Totara Grove Orchard, New Zealand. 'CABp Fuji' was asexually propagated at Totara Grove Orchard in 1995, and has been shown to remain true to type over successive generations.

BRIEF SUMMARY OF THE INVENTION

'CABp Fuji' is a new and distinct apple tree notable for its large, attractive fruit, having a pronounced stripe and superior color as compared to its parent 'Nagafu-6' and other known cultivars.

BRIEF DESCRIPTION OF THE PHOTOGRAPH

DETAILED BOTANICAL DESCRIPTION

Figure 1:
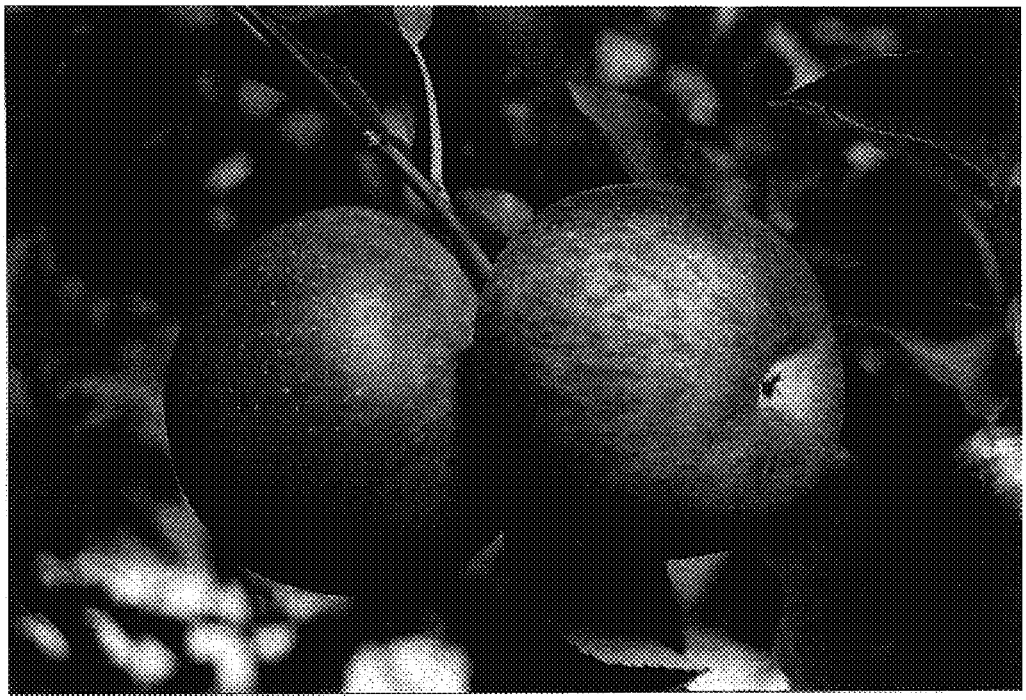
FIG. 1 shows the fruit and leaves of the new cultivar.
Figure 2:
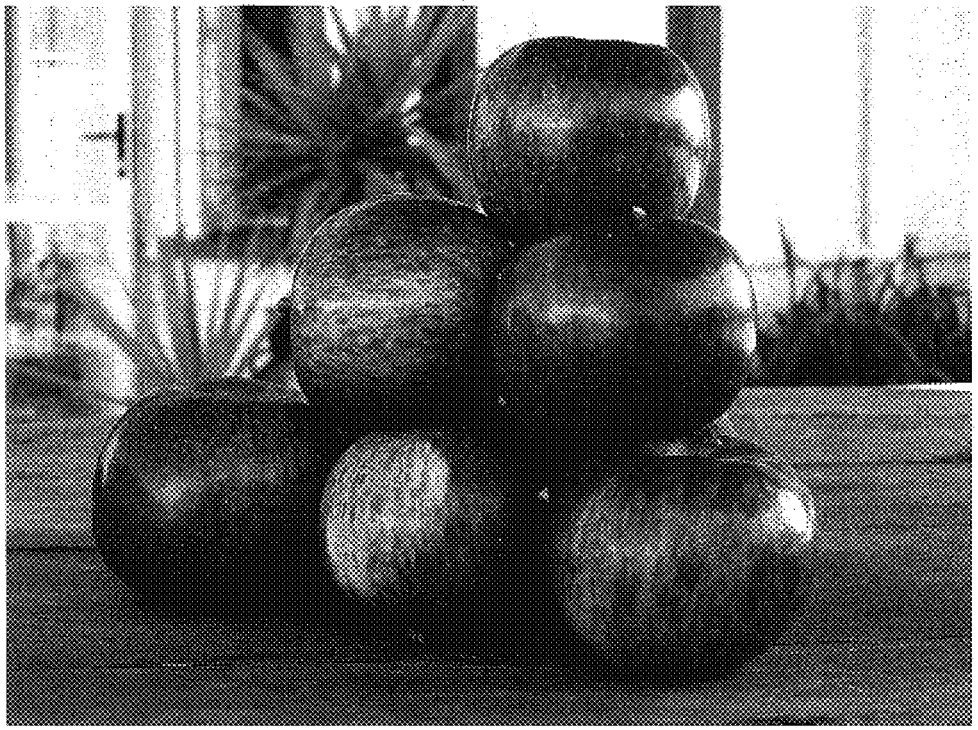
FIG. 2 shows the fruit of the new cultivar.
Figure 3:
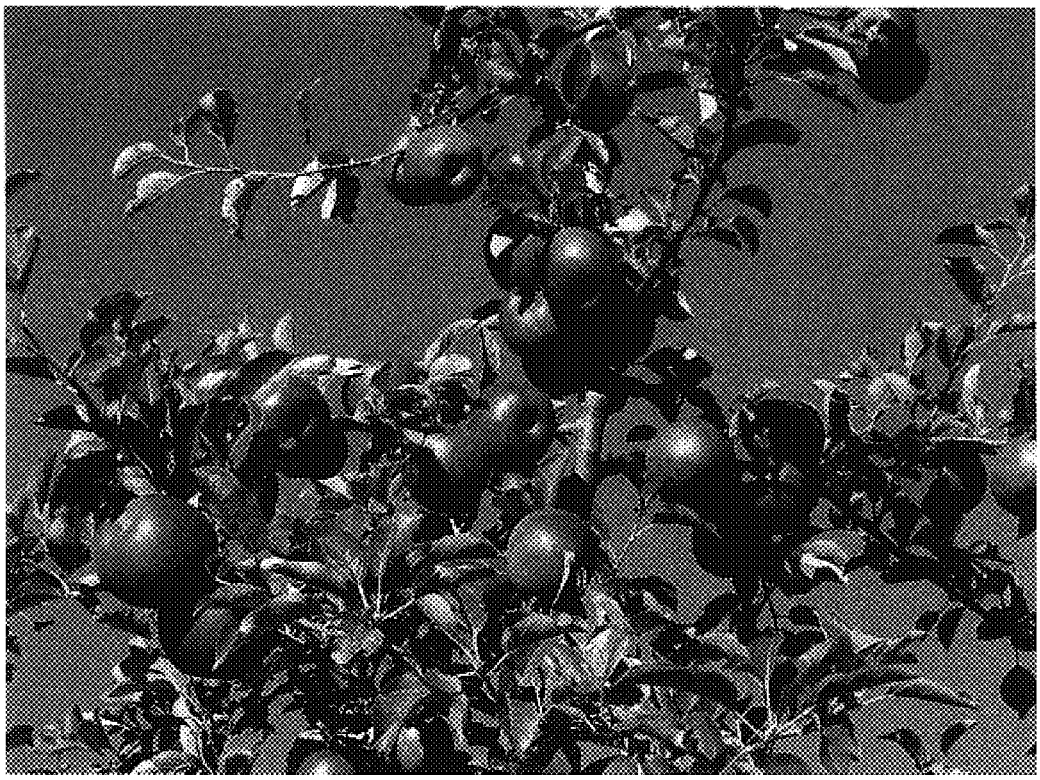
FIG. 3 shows the fruit and branches of the new cultivar.

The following detailed botanical description is based on observations of four year old trees made during the 1999/2000 growing season at Totara Grove Orchard, New Zealand. All colors are described according to The Royal Horticultural Society Colour Chart. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:
- *Vigor.*—Weak.
- *Type.*—Ramified.
- *Habit.*—Spreading.
- *Size.*—Height, 3.6 m; diameter, 3.5 m at 1.5 m high.
- *Trunk.*—Diameter 10 cm at 20 cm above graft union; bark texture smooth to medium; Color variegated greyed-orange 165 A, 177A; lenticels 4 mm long, 3 mm wide, color greyed-yellow 161A, concentration 4 per $cm^2$.
- *Branches.*—Diameter 42 mm (5 year old branch, 50 cm from trunk); Crotch angle 0° to 30° ; Greyed-brown 199A; lenticels 4 mm long, 1 mm wide, color greyed-yellow 161A, concentration 8 per $cm^2$.

Dormant one year old shoot:
- *Pubescence on upper half.*—Medium.
- *Size.*—Thickness (center diameter of middle internode) 5 cm; length 40 cm.
- *Length of internode (middle third of one year old shoot).*—Medium, 3.0 cm to 3.5 cm.
- *Color.*—Greyed-orange 174A.

Flower:
- *Bud.*—Length 0.9 cm; diameter 0.6 cm; body green 146C; tip pink 62A.
- *Flower size.*—Diameter 4.3 cm to 4.4 cm.
- *Quantity per cluster.*—4 to 6.

*Petals.*—Quantity per flower 5; touching; length 1.7 cm; width 1.1 cm; margin smooth; upper surface white 155D; lower surface white 155D when fully open.

*Sepals.*—Length 0.4 cm; width 0.2 cm; color green 146C.

*Pistil.*—Length 0.8 cm to 1.0 cm; green 145C.

*Anthers.*—Length 0.5 cm; pollen yellow 1A.

*Bloom period.*—Medium to late season; first bloom October 1, full bloom October 7 at Totara Grove Orchard, New Zealand.

Leaf:

*Attitude in relation to shoot.*—Upward.

*Leaf size.*—Length 8.5 cm to 9.0 cm; width 6.0 cm.

*Leaf shape.*—Ovate; apex acuminate; base obtuse.

*Ratio: length/width.*—Small to medium.

*Shape of margins.*—Crenate.

*Color.*—Upper surface green N134C; lower surface yellow-green 148C.

Fruit:

*Size.*—Large; length 72 mm to 74 mm; width 71 mm to 73 mm; weight 175 g.

*Ratio: height/width.*—Small.

*Position of maximum width.*—In middle.

*Shape.*—Globose.

*Ribbing.*—Absent or very weak.

*Crowning at calyx end.*—Absent or very weak.

*Aperture of eye.*—Closed.

*Size of eye.*—Small.

*Length of sepal.*—Short to medium.

*Eye basin.*—Width 3.2 cm; depth 1.1 cm.

*Stalk.*—Diameter 3.5 mm; length 23 mm; color greyed-red 178B.

*Stalk cavity.*—Depth 1.3 cm; width 3.5 cm.

*Bloom of skin.*—Absent or very weak.

*Greasiness of skin.*—Absent or very weak.

*Ground color of skin.*—Greyed-yellow 162C.

*Amount of overcolor of skin.*—Very High.

*Color of overcolor of skin.*—Greyed-red 180A.

*Intensity of overcolor.*—Medium.

*Pattern of overcolor.*—Solid flush with stripes.

*Amount of russet around eye basin.*—Absent or very low.

*Amount of russet on cheeks.*—Absent or very low.

*Amount of russet around stalk cavity.*—Absent or very low.

*Size of lenticels.*—Medium-large.

*Flesh.*—Firmness 6.7 kg to 7.0 kg; white 155B; 13.1°brix at optimal picking time.

*Fruit in cross section: aperture of locules.*—Fully open.

*Seeds.*—Avg. 9 per fruit; greyed-orange 166A.

*Time of maturity for consumption.*—Medium to late; mid-April to Early May at Totara Grove Orchard, New Zealand.

*Yield.*—Similar to 'Fuji'.

*Use.*—Processing, fresh domestic and export.

*Resistance to known diseases.*—None.

*Storageability.*—Similar to 'Fuji'.

It is claimed:

1. We claim a new and distinct apple tree substantially as shown and described herein.

* * * * *